United States Patent [19]

Kikumoto et al.

[11] 4,339,580
[45] Jul. 13, 1982

[54] PIPERAZINYLALKOXYINDANES AND ACID ADDITION SALTS THEREOF

[75] Inventors: Ryoji Kikumoto, Machida; Akihiro Tobe, Kawasaki; Harukazu Fukami; Mitsuo Egawa, both of Yokohama, all of Japan

[73] Assignee: Mitsubishi Chemical Industries, Limited, Tokyo, Japan

[21] Appl. No.: 157,341

[22] Filed: Jun. 9, 1980

[30] Foreign Application Priority Data

Jun. 26, 1979 [JP] Japan .................................. 54-80505
Mar. 10, 1980 [JP] Japan .................................. 55-30062

[51] Int. Cl.$^3$ ................. C07D 401/04; C07D 241/04; A61K 31/495

[52] U.S. Cl. .................................. 544/360; 424/250; 544/365; 544/394

[58] Field of Search ........................ 544/360, 365, 394

[56] References Cited

U.S. PATENT DOCUMENTS 3,476,767 11/1969 Bencze ................................ 544/365
4,271,161 6/1981 Teulon ................................ 544/394

Primary Examiner—Donald G. Daus
Assistant Examiner—James H. Turnipseed
Attorney, Agent, or Firm—Oblon, Fisher, Spivak, McClelland & Maier

[57] ABSTRACT

Piperazinylalkoxyindanes and their pharmaceutically acceptable acid addition salts which have anti-anxiety activity and are effective as sedatives.

4 Claims, No Drawings

PIPERAZINYLALKOXYINDANES AND ACID ADDITION SALTS THEREOF

BACKGROUND OF THE INVENTION

FIELD OF THE INVENTION

This invention relates to piperazinylalkoxyindanes and their pharmaceutically acceptable acid addition salts. More particularly, it relates to novel piperazinylalkoxyindanes having anti-anxiety activity and effective as sedatives.

SUMMARY OF THE INVENTION

The compounds of this invention can be represented by the formula (I):

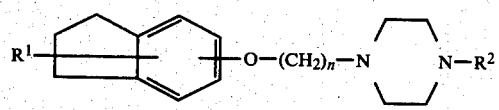

wherein n is an integer of 3 or 4; $R^1$ is hydrogen, halogen, alkyl, alkoxy, hydroxy, phenyl or nitro; and $R^2$ is a phenyl or pyridyl group which may optionally have at least one substituent selected from the group consisting of halogen, trifluoromethyl, alkoxy and alkylcarbonyl.

Also encompassed within this invention are the pharmaceutically acceptable acid addition salts thereof.

The compounds of this invention can be used effectively as sedatives having anti-anxiety effect.

DETAILED DESCRIPTION OF THE PREFERRED EMBODIMENTS

This invention relates to piperazinylalkoxyindanes of the formula (I):

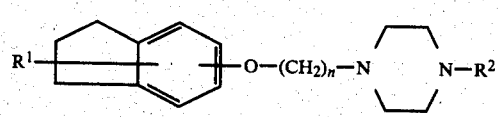

wherein n is an integer of 3 or 4; $R^1$ is hydrogen, halogen, alkyl, alkoxy, hydroxy, phenyl or nitro; and $R^2$ is a phenyl or pyridyl group which may optionally have at least one substituent selected from the group consisting of halogen, trifluoromethyl, alkoxy and alkylcarbonyl.

The term "halogen" used herein includes fluorine, chlorine, bromine and the like. The term "alkyl" includes lower alkyl groups having 1 to 5 carbon atoms such as methyl, ethyl, propyl, isopropyl and butyl. The term "alkoxy" includes lower alkoxy groups having 1 to 5 carbon atoms such as methoxy, ethoxy, propoxy and butoxy. Similarly the term "alkylcarbonyl" includes lower alkylcarbonyl groups having 2 to 6 carbon atoms such as acetyl, propionyl, butyryl and isobutyryl.

The position of $R^1$ and piperazinylalkoxy on the indane ring as well as the position of the substituent, if any, on $R^2$ are not critical.

The compounds of the invention may be prepared by reacting a haloalkoxyindane of the formula:

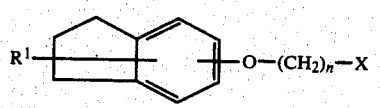

wherein n and $R^1$ are as defined above and X is halogen, with a piperazine of the formula:

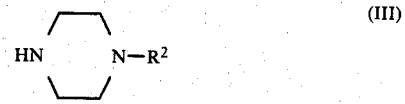

wherein $R^2$ is as defined above.

While the haloalkoxyindane and the piperazine react in equimolecular amounts, usually the latter is used in excess so that the reaction proceeds smoothly. In general the piperazine is used in an amount of 1 to 10 moles per mole of haloalkoxyindane.

Although the reaction proceeds satisfactorily in the absence of solvent, any inert solvent may be employed, if desired, in order to achieve a smooth progress of the reaction. For this purpose, water, dioxane, tetrahydrofuran, dimethylformamide, dimethyl sulfoxide, a lower alcohol and the mixture of two or more of these solvents may be used as the solvent.

The reaction temperature is not critical, but usually in the range of from room temperature to 150° C.

The reaction time varies depending on the reaction temperature, the reactivities of the starting materials and the particular solvent, and is usually in the range of from 10 minutes to 20 hours.

A base may be added in order to bind the hydrogen halide formed in the reaction, thereby accelerating the reaction. Examples of the base are inorganic bases such as potassium hydroxide, potassium carbonate, sodium hydroxide, sodium hydrogen carbonate and sodium carbonate as well as organic tertiary amines such as pyridine and triethylamine. Usually the base is added in an amount of 1 to 5 moles per mole of the piperazine.

In order to obtain a desired acid addition salt of the compound of formula (I), after completion of the reaction the reaction mixture is distilled and/or washed with water to remove the excess amines and solvent, whereupon an aqueous solution of a strong base such as sodium hydroxide or potassium hydroxide is added to give the free piperazinylalkoxyindane, which is then extracted with a suitable solvent, e.g., ether, chloroform, benzene or toluene. The extract is then neutralized with the appropriate acid to give the desired acid addition salt.

Specific examples of the compounds of the invention are:

5-[3-(4-phenyl-1-piperazinyl)propoxy]indane,
5-[4-(4-phenyl-1-piperazinyl)butoxy]indane,
4-[3-(4-phenyl-1-piperazinyl)propoxy]indane,
4-[4-(4-phenyl-1-piperazinyl)butoy]indane,
5-{3-[4-(4-fluorophenyl)-1-piperazinyl]propoxy}indane,
5-{3-[4-(3-fluorophenyl)-1-piperazinyl]propoxy}indane,
5-{3-[4-(2-fluorophenyl)-1-piperazinyl]propoxy}indane,
4-{3-[4-(4-fluorophenyl)-1-piperazinyl]propoxy}indane,
4-{3-[4-(3-fluorophenyl)-1-piperazinyl]propoxy}indane,
4-{3-[4-(2-fluorophenyl)-1-piperazinyl]propoxy}indane,
5-{4-[4-(4-fluorophenyl)-1-piperazinyl]butoxy}indane,
5-{4-[4-(3-fluorophenyl)-1-piperazinyl]butoxy}indane,
5-{4-[4-(2-fluorophenyl)-1-piperazinyl]butoxy}indane,
4-{4-[4-(4-fluorophenyl)-1-piperazinyl]butoxy}indane,
5-{3-[4-(4-chlorophenyl)-1-piperazinyl]propoxy}indane,
5-{3-[4-(3-chlorophenyl)-1-piperazinyl]propoxy}indane, 5-{3-[4-(2-chlorophenyl)-1-piperazinyl]propoxy}indane,
4-{3-[4-(4-chlorophenyl)-1-piperazinyl]propoxy}indane,
4-{3-[4-(3-chlorophenyl)-1-piperazinyl]propoxy}indane,
4-{3-[4-(2-chlorophenyl)-1-piperazinyl]propoxy}indane,
5-{4-[4-(4-chlorophenyl)-1-piperazinyl]butoxy}indane,
5-{4-[4-(3-chlorophenyl)-1-piperazinyl]butoxy}indane,
5-{4-[4-(2-chlorophenyl)-1-piperazinyl]butoxy}indane,
4-{4-[4-(4-chlorophenyl)-1-piperazinyl]butoxy}indane,
4-{4-[4-(3-chlorophenyl)-1-piperazinyl]butoxy}indane,
5-{3-[4-(4-trifluoromethylphenyl)-1-piperazinyl]propoxy}indane,
5-{3-[4-(3-trifluoromethylphenyl)-1-piperazinyl]propoxy}indane,
5-{3-[4-(2-trifluoromethylphenyl)-1-piperazinyl]propoxy}indane,
4-{3-[4-(4-trifluoromethylphenyl)-1-piperazinyl]propoxy}indane,
4-{3-[4-(3-trifluoromethylphenyl)-1-piperazinyl]propoxy}indane,
4-{3-[4-(2-trifluoromethylphenyl)-1-piperazinyl]propoxy}indane,
5-{4-[4-(4-trifluoromethylphenyl)-1-piperazinyl]butoxy}indane,
5-{4-[4-(3-trifluoromethylphenyl)-1-piperazinyl]butoxy}indane,
5-{4-[4-(2-trifluoromethylphenyl)-1-piperazinyl]butoxy}indane,
4-{4-[4-(4-trifluoromethylphenyl)-1-piperazinyl]butoxy}indane,
4-{4-[4-(3-trifluoromethylphenyl)-1-piperazinyl]butoxy}indane,
4-{4-[4-(2-trifluoromethylphenyl)-1-piperazinyl]butoxy}indane,
5-{3-[4-(4-methoxyphenyl)-1-piperazinyl]propoxy}indane,
5-{3-[4-(3-methoxyphenyl)-1-piperazinyl]propoxy}indane,
5-{3-[4-(2-methoxyphenyl)-1-piperazinyl]propoxy}indane,
4-{3-[4-(4-methoxyphenyl)-1-piperazinyl]propoxy}indane,
4-{3-[4-(3-methoxyphenyl)-1-piperazinyl]propoxy}indane,
4-{3-[4-(2-methoxyphenyl)-1-piperazinyl]propoxy}indane,
5-{4-[4-(4-methoxyphenyl)-1-piperazinyl]butoxy}indane,
4-{4-[4-(4-methoxyphenyl)-1-piperazinyl]butoxy}indane,
5-{3-[4-(4-ethoxyphenyl)-1-piperazinyl]propoxy}indane,
5-{3-[4-(4-propoxyphenyl)-1-piperazinyl]propoxy}indane,
5-{3-[4-(4-acetoxyphenyl)-1-piperazinyl]propoxy}indane,
4-{3-[4-(4-acetoxyphenyl)-1-piperazinyl]propoxy}indane,
5-{4-[4-(4-acetoxyphenyl)-1-piperazinyl]butoxy}indane,
5-{3-[4-(2-pyridyl)-1-piperazinyl]propoxy}indane,
5-{3-[4-(3-pyridyl)-1-piperazinyl]propoxy}indane,
5-{3-[4-(4-pyridyl)-1-piperazinyl]propoxy}indane,
5-{4-[4-(2-pyridyl)-1-piperazinyl]butoxy}indane,
4-{3-[4-(2-pyridyl)-1-piperazinyl]propoxy}indane,
4-{4-[4-(2-pyridyl)-1-piperazinyl]butoxy}indane,
5-{3-[4-(4-chloro-2-pyridyl)-1-piperazinyl]propoxy}indane,
6-fluoro-5-[3-(4-phenyl-1-piperazinyl)propoxy]indane,
6-fluoro-5-[4-(4-phenyl-1-piperazinyl)butoxy]indane,
6-methyl-5-[3-(4-phenyl-1-piperazinyl)propoxy]indane,
6-chloro-5-[3-(4-phenyl-1-piperazinyl)propoxy]indane,
6-fluoro-5-{3-[4-(4-fluorophenyl)-1-piperazinyl]propoxy}indane,
6-fluoro-5-{3-[4-(3-fluorophenyl)-1-piperazinyl]propoxy}indane,
6-chloro-5-{3-[4-(2-fluorophenyl)-1-piperazinyl]propoxy}indane,
6-methoxy-5-{3-[4-(4-fluorophenyl)-1-piperazinyl]propoxy}indane,
6-ethoxy-5-{3-[4-(3-fluorophenyl)-1-piperazinyl]propoxy}indane,
1-ethyl-5-{3-[4-(2-fluorophenyl)-1-piperazinyl]propoxy}indane,
6-fluoro-5-{4-[4-(4-fluorophenyl)-1-piperazinyl]buthoxy}indane,
6-chloro-5-{4-[4-(3-fluorophenyl)-1-piperazinyl]buthoxy}indane,
6-propoxy-5-{4-[4-(2-fluorophenyl)-1-piperazinyl]buthoxy}indane,
1-phenyl-5-{3-[4-(4-fluorophenyl)-1-piperazinyl]propoxy}indane,
6-fluoro-5-{3-[4-(4-chlorophenyl)-1-piperazinyl]propoxy}indane,
6-fluoro-5-{3-[4-(3-chlorophenyl)-1-piperazinyl]propoxy}indane,
6-hydroxy-5-{3-[4-(3-chlorophenyl)-1-piperazinyl]propoxy}indane,
6-nitro-4-{3-[4-(4-chlorophenyl)-1-piperazinyl]propoxy}indane,
6-nitro-5-{3-[4-(3-chlorophenyl)-1-piperazinyl]propoxy}indane,
6-methoxy-5-{3-[4-(2-chlorophenyl)-1-piperazinyl]propoxy}indane,
6-methoxy-5-{4-[4-(4-chlorophenyl)-1-piperazinyl]buthoxy}indane,
6-chloro-5-{4-[4-(3-chlorophenyl)-1-piperazinyl]buthoxy}indane,
6-chloro-5-{4-[4-(2-chlorophenyl)-1-piperazinyl]buthoxy}indane,
6-ethyl-5-{4-[4-(4-chlorophenyl)-1-piperazinyl]buthoxy}indane,
6-chloro-4-{4-[4-(3-chlorophenyl)-1-piperazinyl]buthoxy}indane,
6-chloro-5-{3-[4-(4-trifluoromethylphenyl)-1-piperazinyl]propoxy}indane,
6-fluoro-5-{3-[4-(3-trifluoromethylphenyl)-1-piperazinyl]propoxy}indane,
6-methyl-5-{3-[4-(2-trifluoromethylphenyl)-1-piperazinyl]propoxy}indane,
6-methoxy-5-{3-[4-(4-trifluoromethylphenyl)-1-piperazinyl]propoxy}indane,
1-ethyl-5-{3-[4-(3-trifluoromethylphenyl)-1-piperazinyl]propoxy}indane,
6-methyl-5-{3-[4-(3-trifluoromethylphenyl)-1-piperazinyl]propoxy}indane,
6-fluoro-5-{4-[4-(4-trifluoromethylphenyl)-1-piperazinyl]buthoxy}indane,
6-chloro-5-{4-[4-(3-trifluoromethylphenyl)-1-piperazinyl]buthoxy}indane,
6-nitro-5-{4-[4-(2-trifluoromethylphenyl)-1-piperazinyl]buthoxy}indane, 6-methoxy-4-{4-[4-(4-trifluoromethylphenyl)-1-piperazinyl]buthoxy}indane,
6-methyl-5-{3-[4-(4-fluorophenyl)-1-piperazinyl]propoxy}indane,
6-chloro-5-{3-[4-(4-fluorophenyl)-1-piperazinyl]propoxy}indane,
6-chloro-5-{3-[4-(3-chlorophenyl)-1-piperazinyl]propoxy}indane,
6-methoxy-5-[3-(4-phenyl-1-piperazinyl)propoxy]indane,
6-methoxy-5-{3-[4-(3-chlorophenyl)-1-piperazinyl]propoxy}indane,
6-hydroxy-5-[3-(4-phenyl-1-piperazinyl)propoxy]indane,
6-hydroxy-5-{3-[4-(4-fluorophenyl)-1-piperazinyl]propoxy}indane,
6-nitro-5-[3-(4-phenyl-1-piperazinyl)propoxy]indane,
6-nitro-5-{3-[4-(4-fluorophenyl)-1-piperazinyl]propoxy}indane,
1-ethyl-5-{3-[4-(4-fluorophenyl)-1-piperazinyl]propoxy}indane, and
1-phenyl-5-[3-(4-phenyl-1-piperazinyl)propoxy]indane.

Pharmaceutically acceptable acid addition salts of the above-identified compounds also fall within the invention. The acids which are used to form addition salts include inorganic acids such as hydrochloric, hydrobromic, sulfuric, phosphoric and nitric acid as well as organic acids such as acetic, succinic, adipic, propionic, tartaric, fumaric, maleic, oxalic, citric, benzoic, toluenesulfonic and methanesulfonic acid.

As previously mentioned, the compounds according to the invention possess anti-anxiety activity.

The anti-anxiety effects of the compounds were demonstrated in the following manner:

As controls, chlorodiazepoxide which is known as an anti-anxiety agent or minor tranquilizer and a known Compound 40 were used. The results are summarized in terms of 50% effective dose ($ED_{50}$, mg/kg P.O.) in Table 1 below.

The animals used were ddy male mice (weighing 20 to 22 g) and they were tested for anti-fighting and anti-morphine actions as indications of anti-anxiety action. The anti-fighting activity of the test compound was evaluated by its suppressing or taming effect against fighting which was developed by applying an electric shock (28 V-DC, 4–5 mA, 3 min.) through a grid to the foot of the animal [R. E. Tedeschi, D. H. Tedeschi, A. Mucha, L. Cook, P. A. Mattis, E. J. Fellows, J. Pharmacol. exp. Therap., 125, 28 (1959)] The anti-morphine activity was evaluated according to the method of Takagi et al. by the suppressing effect against a tail reaction induced by administration of 20 mg/kg i.p. of morphine [H. Takagi, T. Kamioka, S. Kobayashi, Y. Suzuki and K. Tachikawa, Japanese J. of Pharmacology, 66, 107 (1970)].

Muscle relaxant action was evaluated by a traction test [S. Courvoisier, R. Ducrot, L. Julou, "Psychotropic Drugs" Ed. by S. Garattini, V. Ghetti, p. 313 (Elsevier) 1957].

The values for $LD_{50}$ were calculated by the Litchfield-Wilcoxon method [J. T. Litchfield and F. Wilcoxon, J. Pharmacol. exp. Therap., 96, 99 (1949)].

As Table 1 shows, Compounds 1, 4, 5, 17, 18, 19, 21, 24 and 30 were found to have anti-anxiety activities superior to those of chlorodiazepoxide and Compound 40 used as controls. All of the Compounds showed a lower toxicity and a weaker muscle relaxant action than chlorodiazepoxide so that these compounds are presumed to be a drug of high safety.

TABLE 1

| No. | Compound | $ED_{50}$ (mg/kg PO) Anti-morphine activity | Taming effect | Traction test | $LD_{50}$ (mg/kg PO) |
|---|---|---|---|---|---|
| 1. | [indane-O(CH₂)₃N-piperazine-N-phenyl] | 6.3 | 6.6 | 14.1 | >1,500 |
| 4. | [indane-O(CH₂)₃N-piperazine-N-C₆H₄-F] | 6.0 | 7.5 | 28.0 | >2,000 |
| 5. | [indane-O(CH₂)₄N-piperazine-N-C₆H₄-F] | 11.1 | 12.0 | 21.5 | >1,100 |
| 17. | [indane-O(CH₂)₃N-piperazine-N-C₆H₄-Cl] | 15.5 | 12.6 | 45 | >2,000 |
| 18. | [F-indane-O(CH₂)₃N-piperazine-N-phenyl] | 10.6 | 2.9 | 14.5 | >2,000 |
| 19. | [F-indane-O(CH₂)₃N-piperazine-N-C₆H₄-F] | 12.5 | 1.0 | 17.5 | >2,000 |
| 21. | [F-indane-O(CH₂)₃N-piperazine-N-C₆H₄-Cl] | 13.8 | 14.5 | 88 | 1,500–2,000 |

TABLE 1-continued

| No. | Compound | ED$_{50}$ (mg/kg PO) Anti-morphine activity | Taming effect | Traction test | LD$_{50}$ (mg/kg PO) |
|---|---|---|---|---|---|
| 24. | (indane)-CH$_3$, O(CH$_2$)$_3$N(piperazinyl)-phenyl | 16.0 | 8.5 | 46 | >2,000 |
| 30. | (indane)-OCH$_3$, O(CH$_2$)$_3$N(piperazinyl)-phenyl-F | 10.2 | 13.0 | 12.5 | >1,000 |
| 40. | (indane)-CO(CH$_2$)$_3$N(piperazinyl)-phenyl-F | 15.5 | 20.0 | 57.0 | 1,000–1,500 |
| | Chlorodiazepoxide | 13.0 | 12.5 | 8.3 | 720 |

Particularly valuable compounds having high anti-anxiety activity are the compounds of Formula (I) wherein n is an integer of 3 or 4; $R^1$ is hydrogen, fluorine, chlorine, $C_1$–$C_3$ alkyl or $C_1$–$C_3$ alkoxy; when $R^1$ is hydrogen $R^2$ is an unsubstituted or substituted phenyl or pyridyl group, said substituent on the benzene or pyridine ring, if any, being halogen, particularly fluorine or chlorine, $C_1$–$C_3$ alkoxy, $C_2$–$C_4$ alkylcarbonyl or trifluoromethyl; and when $R^1$ is fluorine, chlorine, $C_1$–$C_3$ alkyl or $C_1$–$C_3$ alkoxy $R^2$ is unsubstituted or substituted phenyl, said substituent on the benzene ring, if any, being halogen, particularly fluorine or chlorine, $C_1$–$C_3$ alkoxy or trifluoromethyl. Preferably, the piperazinylalkoxy group are attached to the indane ring at the 4- or 5-position of the latter.

The following compounds exhibit particularly effective anti-anxiety activity:

5-[3-(4-phenyl-1-piperazinyl)propoxy]indane,
4-[3-(4-phenyl-1-piperazinyl)propoxy]indane,
5-[4-(4-phenyl-1-piperazinyl)butoxy]indane,
5-3-[4-(4-fluorophenyl)-1-piperazinyl]propoxy indane,
5-4-[4-(4-fluorophenyl)-1-piperazinyl]butoxy indane,
4-3-[4-(4-fluorophenyl)-1-piperazinyl]propoxy indane,
5-3-[4-(3-trifluoromethylphenyl)-1-piperazinyl]propoxy indane,
6-fluoro-5-[3-(4-phenyl-1-piperazinyl)propoxy]indane,
6-methyl-5-[3-(4-phenyl-1-piperazinyl)propoxy]indane,
6-fluoro-5-{3-[4-(4-fluorophenyl)-1-piperazinyl]propoxy}indane,
6-fluoro-5-{3-[4-(3-chlorophenyl)-1-piperazinyl]propoxy}indane
6-fluoro-5-{4-[4-(4-fluorophenyl)-1-piperazinyl]butoxy}indane
6-methoxy-5-{3-[4-(4-fluorophenyl)-1-piperazinyl]propoxy}indane,
6-chloro-5-[3-(4-phenyl-1-piperazinyl)propoxy]indane,
6-chloro-5-{3-[4-(4-fluorophenyl)-1-piperazinyl]propoxy}indane,
6-methoxy-5-[3-(4-phenyl-1-piperazinyl)propoxy]indane,
6-methoxy-5-{3-[4-(4-fluorophenyl)-1-piperazinyl]propoxy}indane,
1-ethyl-5-{3-[4-(4-fluorophenyl)-1-piperazinyl]propoxy}indane,
and the like.

The compounds according to the invention may be administered by any route and in any appropriate manner.

Oral administration as well as parenteral administration, e.g., subcutaneous, intravenous, intramuscular or intraperitoneal injection are possible.

The dose can be determined depending on the age, condition and weight of the patient, the sorts of concurrent treatment, if any, the frequency of administration and the nature of desired effect. Generally a daily dose of 0.5 to 50 mg/kg, usually 1 to 30 mg/kg-body weight of the active ingredient is administered in one or few portions.

For oral administration the compounds of the invention may be used in the form of tablets, capsules, powders, liquids, elixirs and the like, while for parenteral administration they are used in the form of sterilized liquids such as solutions or suspensions. When the active ingredients are formulated into the above-mentioned form, a solid or liquid, non-toxic pharmaceutical carrier may be incorporated in the formulations.

As an example of the solid carrier, conventional gelatine-type capsules are used. Also the active ingredients may be formulated into tablets or packaged powders with or without an adjuvant.

These capsules, tablets and powders generally contains 5 to 95%, preferably 25 to 90% by weight active ingredient.

Thus a dosage unit for oral administration will contain 5 to 500 mg, preferably 25 to 250 mg of the active ingredient.

As the liquid carrier, for example, water, oils of animals or plant origin such as petroleum, peanut oil, soybean oil, mineral oil and sesame oil and synthetic oils can be used.

In general, preferred liquid carriers are isotonic saline solution, aqueous dextrose or similar sucrose solution, ethylene glycol, propylene glycol and polyethylene glycol. Particularly an injection prepared by use of isotonic saline solution contains 0.5 to 20%, preferably 1 to 10% by weight active ingredient.

Liquids for oral administration are preferably in the form of suspensions or syrups containing 0.5 to 10% by weight active ingredient. In that case, water-like excipients such as pharmaceutical micelles, syrups and flavoring agents can be used as carriers.

As described above, the compounds according to the invention can be used effectively as sedatives having anti-anxiety effects.

Having generally described this invention, a more complete understanding can be obtained by reference to certain preparations and reference examples which are provided herein for purpose of illustration only and are not intended to be limiting in any manner.

PREPARATION 1

A solution of 25.5 g (0.1 mole) of 5-(3-bromopropoxy)indane, 17.8 g (0.11 mole) of N-phenylpiperazine and 15 g of triethylamine in 300 ml of dimethylformamide is heated at 80° C. for 2 hours and then added to 500 ml of aqueous 1 N sodium hydroxide. The mixture is extracted with 2×400 ml of diethyl ether. The combined extracts are washed with saturated sodium chloride solution and dried over anhydrous sodium sulfate. After diethyl ether is distilled off, 50 ml of ethanolic 20% hydrogen chloride solution is added to the residual oil to precipitate crystals, which are then allowed to cool, collected by filtration and finally recrystallized from ethanol to give 35 g (85.6%) of 5-[3-(4-phenyl-1-piperazinyl)propoxy]indane dihydrochloride, m.p. 195°–7° C.

PREPARATION 2

A solution of 27.3 g (0.1 mole) of 5-(3-bromopropoxy)-6-fluoro-indane, 17.8 g (0.11 mole) of N-phenylpiperazine and 15 g of triethylamine in 300 ml of dimethylformamide is heated at 80° C. for 2 hours and then added to 500 ml of aqueous 1 N sodium hydroxide. The mixture is extracted with 2×400 ml of diethyl ether. The combined extracts are washed with saturated sodium chloride solution and dried over anhydrous sodium sulfate. After diethyl ether is distilled off, 50 ml of ethanolic 20% hydrogen chloride solution is added to the residual oil to precipitate crystals, which are then allowed to cool, collected by filtration and finally recrystallized from ethanol to give 36.5 g (85.6%) of 6-fluoro-5-[3-(4-phenyl-1-piperazinyl)propoxy]indane dihydrochloride, m.p. 212°–3° C.

Other compounds are prepared in essentially the same manner as above, and the results of these preparations including the above are summarized in Table 2.

TABLE 2

| No. | Position of piperazinyl-alkoxy group | n | $R^1$ | $R^2$ | Addition salt | m.p. (°C.) | Calculated / Found (%) C | H | N |
|---|---|---|---|---|---|---|---|---|---|
| 1 | 5 | 3 | H |  | 2HCl | 195–7 | 64.54 / 64.31 | 7.39 / 7.38 | 6.84 / 6.92 |
| 2 | 5 | 4 | H |  | 2HCl | 157–9 | 65.24 / 65.35 | 7.62 / 7.58 | 6.62 / 6.56 |
| 3 | 4 | 3 | H |  | 2HCl | 220–4 | 64.54 / 64.51 | 7.39 / 7.32 | 6.84 / 6.87 |
| 4 | 5 | 3 | H | —F | 2HCl | 192–6 | 61.83 / 61.91 | 6.84 / 6.78 | 6.55 / 6.49 |
| 5 | 5 | 4 | H | —F | 2HCl | 168–172 | 62.58 / 62.51 | 7.08 / 7.11 | 6.35 / 6.40 |
| 6 | 4 | 3 | H | —F | 2HCl | 227–8 | 61.83 / 61.91 | 6.84 / 6.73 | 6.55 / 6.39 |
| 7 | 5 | 3 | H | —Cl | 2HCl | 192–3 | 59.53 / 59.51 | 6.59 / 6.51 | 6.31 / 6.28 |
| 8 | 5 | 4 | H | —Cl | 2HCl | 160–3 | 60.66 / 60.59 | 6.86 / 6.90 | 6.15 / 6.10 |
| 9 | 5 | 3 | H |  CF$_3$ | 2HCl | 180–4 | 57.87 / 57.82 | 6.12 / 6.08 | 5.87 / 5.90 |
| 10 | 5 | 4 | H |  CF$_3$ | 2HCl | 173–4 | 58.66 / 58.58 | 6.36 / 6.27 | 5.70 / 5.62 |
| 11 | 4 | 3 | H |  CF$_3$ | 2HCl | 198 | 57.87 / 57.83 | 6.12 / 6.15 | 5.87 / 5.92 |
| 12 | 5 | 3 | H |  | 3HCl | 208–211 | 54.50 / 54.46 | 6.53 / 6.49 | 9.08 / 9.01 |
| 13 | 5 | 3 | H | OCH$_3$  | 2HCl | 183 | 62.87 / 62.76 | 7.34 / 7.28 | 6.37 / 6.29 |

TABLE 2-continued $$R^1 \text{—indane—} O(CH_2)_n\text{—N} \underset{\underset{}{\diagup}}{\diagdown} \text{N—}R^2$$

| No. | Position of piperazinyl-alkoxy group | n | R¹ | R² | Addition salt | m.p. (°C.) | Calculated / Found (%) C | H | N |
|---|---|---|---|---|---|---|---|---|---|
| 14 | 5 | 3 | H | —C₆H₄—OCH₃ | 2HCl | 233–5 | 62.87 / 62.77 | 7.34 / 7.28 | 6.37 / 6.41 |
| 15 | 5 | 3 | H | —C₆H₄—Cl (o) | 2HCl | 241–2 | 59.53 / 59.49 | 6.59 / 6.61 | 6.31 / 6.41 |
| 16 | 5 | 3 | H | —C₆H₄—COCH₃ | 2HCl | 133–4 | 63.85 / 63.90 | 7.14 / 7.07 | 6.21 / 6.11 |
| 17 | 5 | 3 | H | —C₆H₄—Cl (m) | 2HCl | 243–4 | 59.53 / 59.68 | 6.59 / 6.54 | 6.31 / 6.37 |
| 18 | 5 | 3 | 6-F | —C₆H₅ | 2HCl | 213–3 | 61.83 / 61.74 | 6.84 / 6.89 | 6.55 / 6.47 |
| 19 | 5 | 3 | 6-F | —C₆H₄—F | 2HCl | 177 | 59.33 / 59.29 | 6.34 / 6.23 | 6.29 / 6.40 |
| 20 | 5 | 3 | 6-F | —C₆H₄—CF₃ | 2HCl | 177–180 | 55.76 / 55.82 | 5.70 / 5.76 | 5.65 / 5.49 |
| 21 | 5 | 3 | 6-F | —C₆H₄—Cl (m) | 2HCl | 167–172 | 57.22 / 57.29 | 6.11 / 6.01 | 6.07 / 6.21 |
| 22 | 5 | 4 | 6-F | —C₆H₅ | 2HCl | 142–8 | 62.58 / 62.48 | 7.08 / 7.20 | 6.35 / 6.41 |
| 23 | 5 | 4 | 6-F | —C₆H₄—F | 2HCl | 148–151 | 60.13 / 60.09 | 6.58 / 6.43 | 6.10 / 6.02 |
| 24 | 5 | 3 | 6-CH₃ | —C₆H₅ | 2HCl | 198 | 65.24 / 65.18 | 7.62 / 7.51 | 6.62 / 6.74 |
| 25 | 5 | 3 | 6-CH₃ | —C₆H₄—F | 2HCl | 167–170 | 62.58 / 62.66 | 7.08 / 6.98 | 6.35 / 6.42 |
| 26 | 5 | 3 | 6-Cl | —C₆H₅ | 2HCl | 216–220 | 59.53 / 59.48 | 6.59 / 6.61 | 6.31 / 6.25 |
| 27 | 5 | 3 | 6-Cl | —C₆H₄—F | 2HCl | 188–193 | 57.22 / 57.31 | 6.11 / 6.11 | 6.07 / 6.00 |
| 28 | 5 | 3 | 6-Cl | —C₆H₄—Cl (m) | 2HCl | 163–169 | 55.25 / 55.34 | 5.90 / 6.04 | 5.86 / 5.92 |
| 29 | 5 | 3 | 6-OCH₃ | —C₆H₅ | 2HCl | 170–3 | 62.87 / 62.72 | 7.34 / 7.19 | 6.37 / 6.41 |
| 30 | 5 | 3 | 6-OCH₃ | —C₆H₄—F | 2HCl | 159–162 | 60.39 / 60.27 | 6.83 / 6.79 | 6.12 / 6.15 |
| 31 | 5 | 3 | 6-OCH₃ | —C₆H₄—Cl (m) | 2HCl | 180–5 | 58.30 / 58.36 | 6.59 / 6.70 | 5.91 / 6.01 |
| 32 | 5 | 3 | 6-OH | —C₆H₅ | 2HCl | 208–213 | 62.12 / 62.21 | 7.11 / 7.18 | 6.59 / 6.47 |
| 33 | 5 | 3 | 6-OH | —C₆H₄—F | 2HCl | 203–6 | 59.60 / 59.49 | 6.59 / 6.51 | 6.32 / 6.44 |

TABLE 2-continued

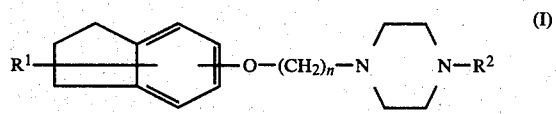

| No. | Position of piperazinyl- alkoxy group | n | R¹ | R² | Addition salt | m.p. (°C.) | Calculated Found (%) C | H | N |
|---|---|---|---|---|---|---|---|---|---|
| 34 | 5 | 3 | 6-OH | -⟨⟩-Cl | 2HCl | 212-7 | 57.46 57.51 | 6.36 6.40 | 6.09 6.12 |
| 35 | 5 | 3 | 6-NO₂ | -⟨⟩ | 2HCl | 235-8 | 58.15 58.21 | 6.43 6.38 | 9.25 9.33 |
| 36 | 5 | 3 | 6-NO₂ | -⟨⟩-F | 2HCl | 203-5 | 55.94 56.03 | 5.97 6.00 | 8.90 8.79 |
| 37 | 5 | 3 | 1-C₂H₅ | -⟨⟩-F | 2HCl | Powder | 63.29 63.34 | 7.30 7.36 | 6.15 6.07 |
| 38 | 5 | 3 | 1-⟨⟩ | -⟨⟩ | 2HCl | 187-191 | 69.27 69.18 | 7.06 7.01 | 5.77 5.72 |
| 39 | 5 | 3 | 1-⟨⟩ | -⟨⟩-F | 2HCl | 150-3 | 66.80 66.72 | 6.61 6.50 | 5.56 5.49 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A piperazinylalkoxyindane represented by the formula:

$$R^1 \text{---}\text{(indane)}\text{---}O\text{---}(CH_2)_n\text{---}N\underset{\diagdown\diagup}{\overset{\diagup\diagdown}{\phantom{N}}}N\text{---}R^2 \quad (I)$$

wherein n is an integer of 3 or 4; R¹ is hydrogen, halogen, alkyl having 1 to 5 carbon atoms, alkoxy having 1 to 5 carbon atoms, hydroxy, phenyl or nitro; and R² is phenyl or pyridyl optionally substituted by halogen, trifluromethyl, alkoxy having 1 to 5 carbon atoms or alkylcarbonyl having 2 to 6 carbon atoms, or a pharmaceutically acceptable acid addition salt thereof.

2. The compound of claim 1, wherein n is an integer of 3 or 4; R¹ is hydrogen; and R² is a phenyl or pyridyl group optionally substituted by halogen, trifluromethyl, $C_1$-$C_5$ alkoxy or $C_2$-$C_6$ alkylcarbonyl, or a pharmaceutically acceptable acid addition salt thereof.

3. The compound of claim 1, wherein n is an integer of 3 or 4; R¹ is halogen, $C_1$-$C_5$ alkyl, $C_1$-$C_5$ alkoxy, hydroxy, phenyl or nitro; and R² is phenyl optionally substituted by halogen, trifluoromethyl or $C_1$-$C_5$ alkoxy, or a pharmaceutically acceptable acid addition salt thereof.

4. The compound of claim 1, wherein n is an integer of 3 or 4; R¹ is hydrogen, fluorine, chlorine, $C_1$-$C_3$ alkyl or $C_1$-$C_3$ alkoxy; when R¹ is hydrogen, R² is phenyl or pyridyl optionally substituted by fluorine, chloride, $C_1$-$C_3$ alkoxy, $C_2$-$C_4$ alkylcarbonyl or trifluoromethyl; when R¹ is fluorine, chlorine, $C_1$-$C_3$ alkyl or $C_1$-$C_3$ alkoxy, R² is phenyl optionally substituted by fluorine, chlorine, $C_1$-$C_3$ alkoxy or trifluoromethyl; and the piperazinylalkoxy group is attached to the indane ring at the 4- or 5-position of the latter, or a pharmaceutically acceptable acid addition salt thereof.

* * * * *